United States Patent [19]

Crainich

[11] Patent Number: 5,180,092
[45] Date of Patent: Jan. 19, 1993

[54] LINEAR SURGICAL STAPLING INSTRUMENT

[76] Inventor: Lawrence Crainich, P.O. Box 996, Charlestown, N.H. 03603

[21] Appl. No.: 831,516

[22] Filed: Feb. 5, 1992

[51] Int. Cl.⁵ .......................................... A61B 17/072
[52] U.S. Cl. ..................................... 227/180; 227/19
[58] Field of Search .................. 227/19, 175, 176, 177, 227/178, 179, 180

[56] References Cited

U.S. PATENT DOCUMENTS

| | | | |
|---|---|---|---|
| 4,402,444 | 9/1983 | Green | 227/19 |
| 4,485,811 | 12/1984 | Chernousov et al. | 227/19 |
| 4,633,861 | 1/1987 | Chow et al. | 227/180 |
| 5,014,899 | 5/1991 | Presty et al. | 227/180 |
| 5,065,929 | 11/1991 | Schulze et al. | 227/180 |
| 5,074,454 | 12/1991 | Peters | 227/178 |

Primary Examiner—Frank T. Yost
Assistant Examiner—Scott A. Smith
Attorney, Agent, or Firm—Bachman & LaPointe

[57] ABSTRACT

A linear surgical stapling instrument includes a magazine for holding a plurality of undeformed surgical staples, and an upper jaw carrying the magazine and having opposed distal and proximal ends. An anvil is formed with staple-deforming pockets, and a lower jaw carries the anvil. In particular the lower jaw is formed as a channel defined by an inverted U-shaped cross section. The anvil is formed on the outer surface of the back of the U-shaped cross section with the staple deforming pockets stamped or punched therein. Accordingly, the lower jaw can be easily made of metal with known metal-forming techniques, and stamping or punching techniques. In addition, the configuration of the low jaw causes it to resist bending and twisting during the staple deforming operation.

15 Claims, 3 Drawing Sheets

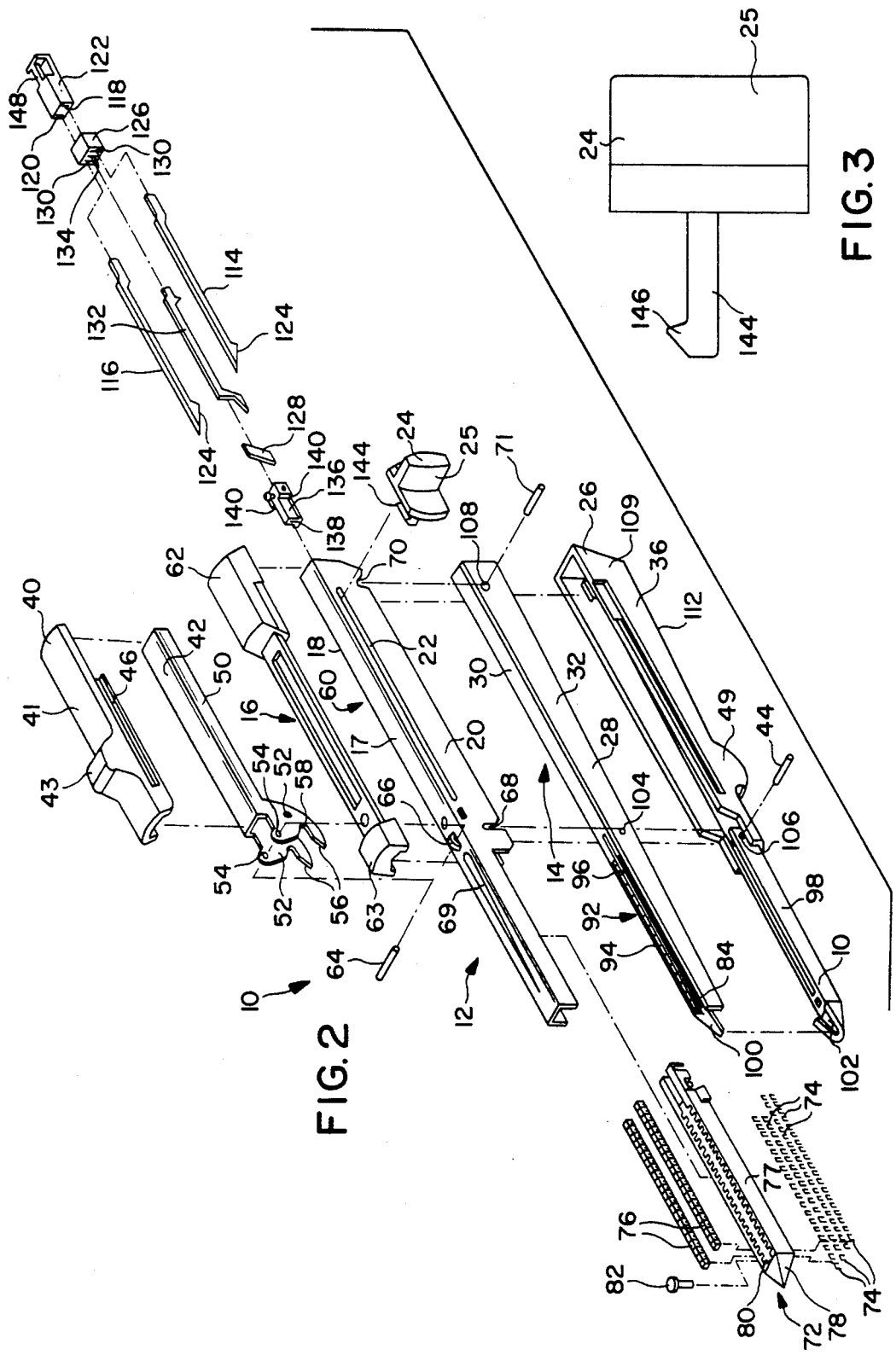

LINEAR SURGICAL STAPLING INSTRUMENT

BACKGROUND OF THE INVENTION

1. Field of the Invention

The present invention relates to a linear anatomic surgical stapling instrument and a surgical staple magazine used therein. More particularly, the invention relates to a gastrointestinal anatomic stapling instrument, which is also known as a gastrointestinal anastomosis instrument or device, for suturing body organs and tissue and to such an instrument that includes components that may be made more easily yet exhibit improved rigidity.

2. Description of the Prior Art

Historically, suturing of a surgical or other wound in organs and tissue has been done by hand. Conventional hand suturing techniques require a high degree of surgical skill. However, expertise in such techniques can vary widely from surgeon to surgeon, thereby resulting in widely varying quality in performance of the concluding steps of an operative procedure. In addition, even very skillful surgeons require a considerable amount of time to suture even relatively small wounds. Therefore, it is possible that an undesirable amount of blood may be lost during the suturing operation.

Accordingly, there has been an increasing tendency in recent years to use surgical staples to suture body organs and tissue after a medical procedure. Surgical staples have been particularly effective in suturing body organs and tissue such as the lung, as well as the esophagus, the stomach, the duodenum, and other body organs in the intestinal tract.

The advent of surgical stapling has provided several marked advantages over known hand suturing techniques. First, since one or more rows of surgical staples are inserted into tissue using a specially adapted instrument that is relatively simple to operate, near uniformity of the closure from one surgeon to the next results. In addition, all staples in the closure are usually inserted simultaneously or in rapid sequence across the entire wound. Therefore, the closure is made very quickly to minimize loss of blood.

The specially adapted instruments for inserting surgical staples are mechanically operated and may be known as anastomosis devices, such as the gastrointestinal anastomosis devices of the type to which this invention relates In such devices, the staples are loaded in one or more elongated rows into a magazine or cartridge. The magazine is then mounted in the device, which includes a mechanism for pushing, or driving, the staples from the magazine through two or more sections of tissue toward a deforming anvil. At the conclusion of the driving operation, the legs of each staple are clamped or bent, by engagement with the anvil, to a closed configuration to complete the suture and join the tissue sections together.

Known gastrointestinal anastomosis stapling instruments usually include a pair of elongated jaws that are maneuvered to position the tissue to be sutured therebetween. The jaws are then clamped tightly together. One of the jaws supports the staple magazine with at least two laterally spaced rows of staples and cooperating staple drivers, and the other jaw supports an anvil with similar complementary rows of staple-forming pockets, each pair of which is aligned with one staple in the cartridge. A reciprocal slide is mounted with one jaw and when advanced therealong longitudinally actuates staple-driving cam surfaces to sequentially depress the staple drivers and drive the staples through the body tissue toward the anvil. Additionally, a knife blade may be advanced with the cam surfaces to slice the tissue between the two rows of deformed staples immediately following the staple deformation so that the adjacent sutured tissue sections can be separated.

As may thus be expected, linear stapling instruments provide many benefits, such as those described above. However, they also have certain drawbacks. For one, many known instruments include a lower jaw made of heavy gauge metal formed into a channel having a C-shaped cross-section with the back of that cross-section at the bottom of the device and the legs bent upwardly and then inwardly toward each other to define a narrow, upwardly facing slot. Staple deforming pockets are then formed in the upwardly facing surfaces of the legs on either side of the slot, thereby to define the anvil. Immediately after staples are driven toward the pockets, the cutting blade may be advanced through the slot to slice tissue that has been sutured with the staples on either side. However, this known lower jaw configuration is difficult to manufacture. Moreover, under high tissue clamping forces between the jaws, the lower jaw is subject to twisting and bending so that the staple-deforming pockets in the anvil may become misaligned with staples in the magazine. Therefore, sutures may not be reliably formed.

Accordingly, further advances and improvements in linear surgical stapling instruments are needed.

SUMMARY OF THE INVENTION

Accordingly, it is an object of the present invention to provide a linear surgical stapling instrument having an improved lower jaw and anvil design that is easily made and has a reduced tendency to twist or bend during staple forming and tissue slicing operations.

These and other objects are achieved by the present invention, which in a preferred embodiment is a linear surgical stapling instrument comprising a magazine for holding a plurality of undeformed surgical staples, and an upper jaw carrying the magazine. A lower metal jaw is formed as a channel having an inverted generally U-shaped cross section defined by an inverted back portion and two leg portions. The outer surface of the back portion defines an anvil having at least one staple-deforming pocket formed therein. The upper and lower jaws are configured removably to mate with each other with the anvil and the magazine in confronting relation. A staple driver is mounted in the upper jaw for driving staples held in the magazine toward the anvil.

Thus the present invention provides a mechanism having a lower jaw that can be easily made, for example, with conventional metal forming techniques and in which staple-deforming pockets can be formed with conventional punching or stamping techniques. Because the lower jaw is formed as a U-shaped channel with its back portion confronting the upper jaw, it has improved rigidity and therefore resists twisting and bending during the staple forming operation.

These and other objects, aspects, features, and advantages of the present invention will become apparent from the following detailed description of the preferred embodiment taken in conjunction with the accompanying drawings.

BRIEF DESCRIPTION OF THE DRAWINGS

FIG. 2 is an exploded perspective view of the linear surgical stapling instrument in accordance with the preferred embodiment of the present invention;

FIG. 3 is a front elevational view of the actuator for the staple driver carried in the upper jaw member of the linear surgical stapling instrument in accordance with the preferred embodiment.

DESCRIPTION OF THE PREFERRED EMBODIMENTS

Figure 1:
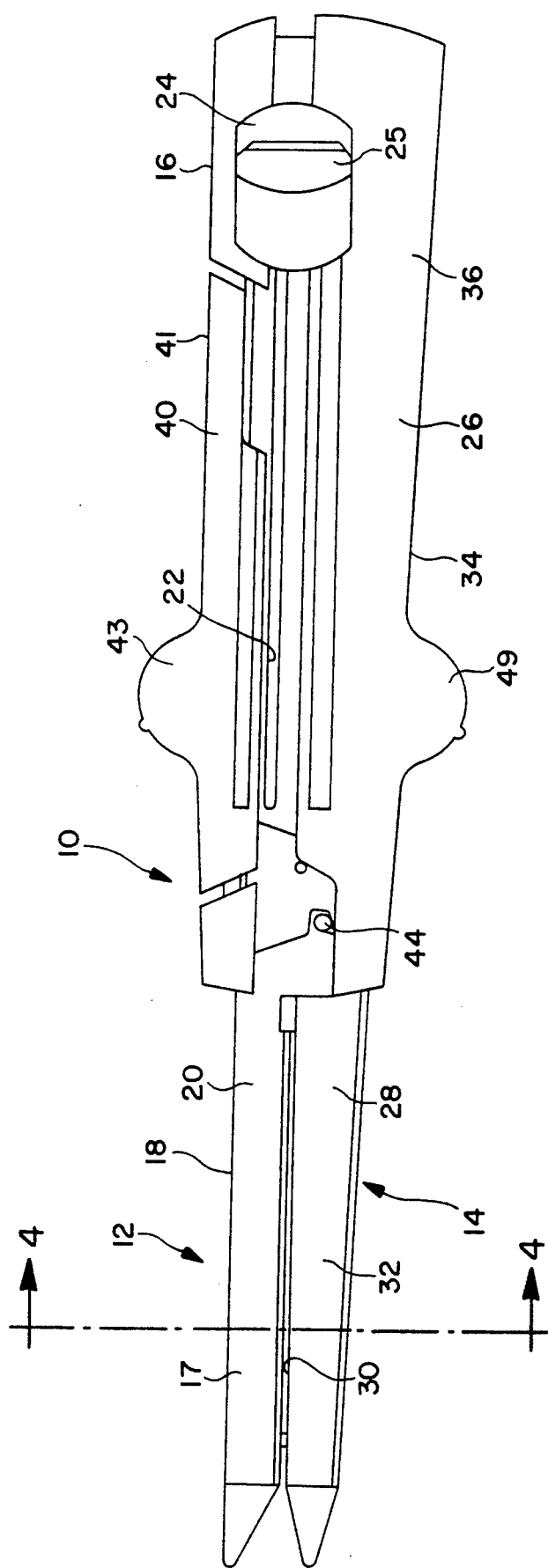
FIG. 1 is a side elevational view of the linear surgical stapling instrument in accordance with the preferred the present invention.

The major components of the linear surgical stapling instrument, generally indicated at 10, in accordance with the preferred embodiment of the subject invention are shown in FIGS. 1 and 2. That instrument includes an upper elongated jaw member 12 and a lower elongated jaw member 14 for gripping therebetween tissue to be sutured. The upper jaw member 12 comprises a top housing 16 which partially encloses an elongated top beam 17 as best seen in FIG. 2. The top beam has an inverted U-shape defined by a top wall 18 and side walls 20 that can be formed of heavy gauge metal. The top beam has an elongated slot 22 in one side wall 20 along which a manually manipulatable actuator 24 may slide as will be described in more detail below. The lower jaw member 14 includes a bottom housing 26 that partially encloses a bottom beam 28, which similarly may be formed of heavy gauge metal, and also has an inverted U-shaped cross section defined by a top or back wall 30 and opposing side walls 32. The bottom housing 26 has a U-shaped cross section defined by a bottom wall 34 and side walls 36. A clamp housing 40 is secured over a clamp bar 42, and the assembly is pivotably mounted on the top beam 17 to clamp the upper and lower jaw members together by gripping a front clamp pin 44 secured in an intermediate region of the bottom beam 28 between its distal and proximal ends.

The respective housings 16, 26, and 40 may be made of molded plastic or metal.

Referring now more specifically to FIG. 2, the components of the preferred embodiment of the linear surgical stapling instrument of the subject invention, including the staple magazine, are shown in detail. Beginning at the top of the Figure, it will be seen that the clamp housing 40 has a top surface 41 that is contoured to fit a surgeon's hand comfortably and that has an enlarged finger grip 43 at a forward end, provided with a non-slip surface. It will be understood that the bottom housing 26 also is formed with a finger grip 49. Similarly, the actuator 24 has a thumb tab 25 that can be engaged by the thumb of the surgeon's other hand.

The clamp housing 40 can be snap-fit onto an elongated handle 50 defining a major portion of the clamp bar 42, which may also be formed of heavy gauge metal. The elongated groove 46 runs longitudinally along the side of the clamp housing.

The clamp bar 42 has spaced parallel hooks 52 at the forward end of the handle 50 formed with pivot pin receiving holes 54 and complementary cam surfaces 56 and clamp pin receiving slots 58 to which the cam surfaces 56 lead.

The top housing 16 provides a cover for a handle portion 60 of the top beam 17. The top housing is therefore shaped to have a palm rest portion 62 and a front upper jaw cover 63 that together complement the clamp housing 40 to provide a smooth upper surface when the clamp bar-housing assembly is closed, as best seen in FIG. 1.

The clamp bar 42 and its housing 40 are mounted for pivoted movement on the top beam 17 by a pivot pin 64 that extends through a lance 66 punched from the top wall 18 of the top beam 17 and is received in the holes 54 in the clamp bar hooks 52.

A stiffening rib 69 may also be provided by being pressed in the top wall 18 of top beam 17 to add strength to the top beam 17 in the region of its distal end.

The side walls 20 of the top beam 17 are formed with clamp pin notches 68, in the intermediate region between the distal and proximal ends, and rear pin notches 70 in the region of the proximal ends. The clamp pin and rear pin notches respectively receive the clamp pin 44 and a rear pin 71 also carried in the bottom beam 28. Both of the clamp and rear pins project beyond the side walls 32 of the bottom beam 28. It will also be appreciated that the side walls 20 of the top beam are spaced by slightly more than the distance between the outer surfaces of the side walls 32 of the bottom beam. Therefore, the top beam can be received over the bottom beam with the clamp and rear pins and notches fit together as described. Accordingly, the clamp pin notches and clamp pin and rear pin notches and rear pin collectively cooperate precisely to position the top and bottom beams with respect to each other for the stapling operation.

The inverted U-shaped channel defined by the top beam 17 receives a disposable staple magazine or cartridge 72, having a housing 78 preferably loaded with four rows of staples 74 and two rows of staple drivers 76. The staple drivers 76 can be driven downwardly in turn sequentially to form the staples 74 in the longitudinal rows to define the suture.

The magazine housing 78 has an opening 80 in one end through which a gap pin 82 extends. The gap pin is received in a small depression or socket 84 in the distal end of the bottom beam 28 of the lower jaw member 14 to align the upper and lower jaw members when mated together and to maintain a minimum gap width between the distal ends of the jaw members.

Figure 4:
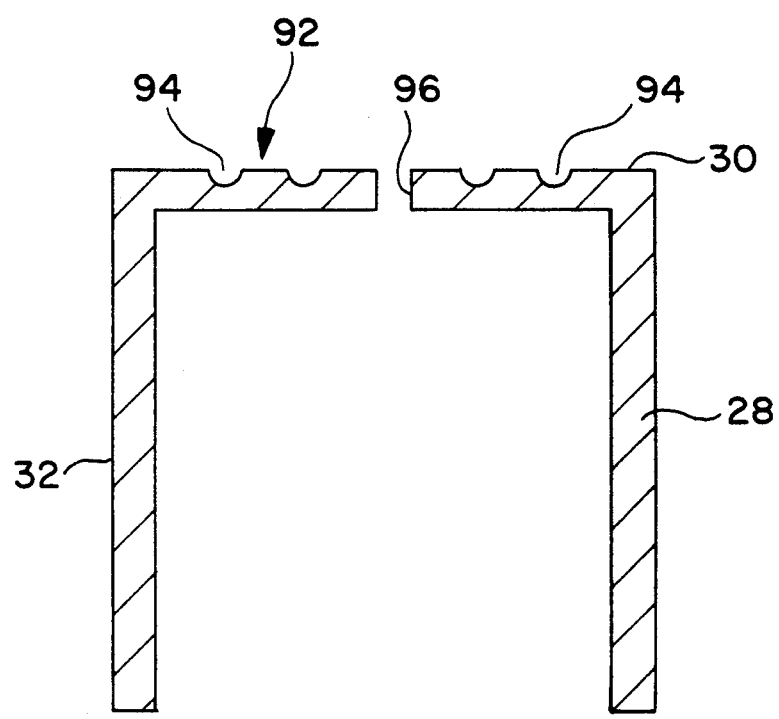
FIG. 4 is a vertical cross-sectional view of the bottom beam comprising the lower jaw member, taken on plane 4—4 in FIG. 1.

The embodiment shown in FIGS. 1 and 2 uses a staple cartridge loaded with metal staples, and the staples are driven into an anvil surface 92 formed on the top or back wall 30 of the bottom beam 28. More particularly, as shown in FIGS. 2 and 4, advantageously the bottom beam is formed as a channel having an inverted, generally U-shaped cross section open at the bottom. This channel configuration can be formed using conventional metal-forming techniques. The anvil surface 92 has linear rows of pairs of staple forming pockets 94 preferably stamped or punched into the outer surface of the top wall 30. The anvil surface 92 also has a longitudinal slot 96 dividing the rows of staple forming pockets 94 of the anvil surface 92.

As seen in FIG. 2, the width of the bottom beam 28 is such that it fits within side walls 36 of the proximal end of the bottom housing 26. The bottom housing also includes an anvil-supporting extension 98 for supporting the distal end of the bottom beam 28. A nose portion 100 of the bottom beam 28 extends from the distal end of the anvil surface 92 and fits into a complementary receiving portion 102 in the bottom housing 26.

The bottom beam 28 is secured in the bottom housing 26 by the clamp pin 44, which extends through holes 104 in the bottom beam 28. The rear pin 71 also extends through rear holes 108 in the bottom beam 28. Finally, the lower surface 112 of the bottom housing 26 is also contoured to be comfortably gripped by the surgeon, and, as noted, has the enlarged finger grip 49, complementary to the finger grip 43 on the clamp housing 40.

The upper and lower jaw members 12 and 14 are mated together with their distal ends abutting each other through the medium of the gap pin 82 and pin socket 84, with the rear pin 71 received on the rear pin notches 70, and the clamp pin 44 received in the clamp pin notches 68. The clamp bar 42 can then be pivoted from its open position to its closed position with the cam surfaces underriding the clamp pin 44, until the clamp pin resides in the clamp pin receiving slots 58 of the clamp bar hooks 52 to clamp the upper and lower jaws together.

FIG. 2 also shows the elements comprising the actuator 24 and its associated mechanism for driving the staples 74 in the magazine 72 toward the anvil surface 92. More particularly, the actuator mechanism includes a left advancer 114 and a right advancer 116, for actuating the staple drivers 76 in the staple magazine, secured in slots 118 and 120 in an actuator mount 122. The right and left advancers each include a cam surface 124 for contacting the staple drivers and forcing them downwardly when the advancers are moved from right to left as shown in the Figure. An optional knife mount 126 may also be operated with the actuator mechanism and is used in conjunction with a cutting blade 128. The knife mount 126 includes outer slots 130 through which the right and left advancers extend before being secured in the actuator mount 122. A knife advancer 132 is secured in a middle slot 134 in the knife mount 126. The angled cutting blade 128, which may be canted upwardly and backwardly, is attached to the lead end of the knife advancer 132. A guide 136 is secured at an intermediate position in the top beam 17 and provides a guiding slot 138 for guiding the knife advancer 132 and guiding slots 140 for guiding the right and left advancers 116 and 114 through the top beam.

The actuator 24 is mounted with the upper jaw member 12 and is connected to the actuator mount 122 to drive all of the advancers as follows.

Referring more particularly to FIGS. 2 and 3, the actuator 24 includes a driving finger 144 that fits through the slot 22 in the top beam 17 and has an upturned lip 146 that is snap-fit behind a connecting bar 148 in the actuator mount 122. When the actuator is fired by being moved from right to left, the cutting blade 128 and cam surfaces 124 are advanced forwardly by the actuator and associated advancers, to drive the staples in the magazine toward the anvil to be deformed thereby, and to advance the cutting blade to cut tissue between the sutures defined by the staples.

Thus, it will be specifically appreciated that the bottom beam 28 of the stapling instrument in accordance with the invention can be formed easily of heavy gauge metal using conventional metal-forming methods. The anvil staple-deforming pockets and slot can be formed with conventional stamping or punching methods. Moreover, the inverted U-shaped channel configuration of the bottom beam causes it to resist twisting and bending when the upper and lower jaws are clamped together and when the actuator is fired to deform the staples and slice tissue with the cutting blade.

Accordingly, the present invention is a marked improvement over the prior art.

Although specific embodiments of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. A linear surgical stapling instrument, comprising:
   (a) a magazine for holding a plurality of undeformed surgical staples;
   (b) an elongated upper jaw carrying said magazine, said upper jaw comprising an elongated top beam having a U-shaped cross-section;
   (c) an elongated lower jaw generally parallel to the upper jaw formed as a channel having an elongated bottom beam with a generally U-shaped cross-section defined by a back portion having an outer surface and two opposing leg portions, the outer surface of said back portion defining an anvil having at least one staple deforming pocket formed therein, said upper and lower jaws being configured to mate with each other and grip therebetween tissue to be sutured, with the top and bottom beams fitting together in parallel relationship with said anvil and said magazine in confronting relation;
   (d) means mounted in said upper jaw for driving staples held in said magazine toward said anvil; and
   (e) a bottom housing having a generally U-shaped cross-section which partially encloses the bottom beam and which forms a hand grip, wherein the bottom beam includes a nose portion which fits into a complementary receiving portion in the bottom housing.

2. The linear surgical stapling instrument according to claim 1, wherein said lower jaw comprises formed metal.

3. The linear surgical stapling instrument according to claim 1, including at least two rows of staple deforming pockets formed in the outer surface of said back portion of said lower jaw and wherein said lower jaw has a slot between said rows of pockets.

4. The linear surgical stapling instrument according to claim 3, further comprising cutting blade means mounted for movement within said slot, wherein said jaws are adapted to clamp tissue therebetween and wherein said cutting blade means is adapted to cut clamped tissue so clamped.

5. A linear surgical stapling instrument according to claim 1, wherein said top beam has an inverted U-shaped cross-section defined by a top wall and side walls, with one of said side walls having an elongated slot therein and including a manually manipulated actuator mechanism slidable in said slot.

6. A linear surgical stapling instrument according to claim 5, wherein the bottom beam has a generally inverted U-shaped cross-section and wherein the side walls of the top beam have a wider spacing than the leg portions of the bottom beam, whereby the top beam is received over the bottom beam.

7. A linear surgical stapling instrument according to claim 6, wherein the bottom beam leg portions carry front and real clamp pins which are received in front and rear pin notches carried in the top beam side walls to precisely position the top and bottom beams with respect to each other.

8. A linear surgical stapling instrument according to claim 7, wherein said front pin notch is formed by a projection portion in the top beam side walls.

9. A linear surgical stapling instrument according to claim 7, including a clamp housing secured over a clamp bar to form a clamp assembly, wherein the clamp assembly is pivotably mounted on the top beam to clamp the upper and lower jaws together, wherein the clamp assembly clamps the front clamp pin to clamp the upper and lower jaws together.

10. A linear surgical stapling instrument according to claim 8, wherein the clamp housing has a top surface that forms a hand grip.

11. A linear surgical stapling instrument according to claim 5, wherein said actuator mechanism includes means for driving staples in the magazine toward said anvil surface.

12. A linear surgical stapling instrument according to claim 11, wherein said means for driving staples includes an advancer having a cam surface which contacts a staple driver in the magazine.

13. A linear surgical stapling instrument according to claim 1, including a clamp housing secured over a clamp bar to form a clamp assembly, wherein the clamp assembly is pivotably mounted on the top beam to clamp the upper and lower jaws together.

14. A linear surgical stapling instrument according to claim 13, including a top housing which partially encloses said top beam.

15. A linear surgical stapling instrument according to claim 1, wherein said bottom housing includes an anvil supporting extension which supports the anvil of said bottom beam.

* * * * *